United States Patent
Liu et al.

(10) Patent No.: US 10,138,274 B2
(45) Date of Patent: *Nov. 27, 2018

(54) CRYSTAL OF CYCLIC PEPTIDE COMPOUND, PREPARATION METHOD FOR SAME AND USES THEREOF

(71) Applicant: SHANGHAI TECHWELL BIOPHARMACEUTICAL CO., LTD, Shanghai (CN)

(72) Inventors: Shidong Liu, Shanghai (CN); Xiusheng Wang, Shanghai (CN); Jicheng Hu, Shanghai (CN); Xiaoming Ji, Shanghai (CN)

(73) Assignee: SHANGHAI TECHWELL BIOPHARMACEUTICAL CO., LTD, Shanghai (CN)

( * ) Notice: Subject to any disclaimer, the term of this patent is extended or adjusted under 35 U.S.C. 154(b) by 44 days.

This patent is subject to a terminal disclaimer.

(21) Appl. No.: 15/314,797

(22) PCT Filed: May 29, 2015

(86) PCT No.: PCT/CN2015/080208
§ 371 (c)(1),
(2) Date: Nov. 29, 2016

(87) PCT Pub. No.: WO2015/180678
PCT Pub. Date: Dec. 3, 2015

(65) Prior Publication Data
US 2017/0198013 A1   Jul. 13, 2017

(30) Foreign Application Priority Data
May 29, 2014 (CN) .......................... 2014 1 0234082

(51) Int. Cl.
| C07K 7/56 | (2006.01) |
| A61K 38/12 | (2006.01) |
| C07K 1/02 | (2006.01) |
| C07K 1/30 | (2006.01) |
| A61K 38/00 | (2006.01) |

(52) U.S. Cl.
CPC ................ *C07K 7/56* (2013.01); *A61K 38/12* (2013.01); *C07K 1/02* (2013.01); *C07K 1/306* (2013.01); *A61K 38/00* (2013.01)

(58) Field of Classification Search
None
See application file for complete search history.

(56) References Cited

FOREIGN PATENT DOCUMENTS

WO    03/018615 A1    3/2003

OTHER PUBLICATIONS

International Search Report, dated Aug. 26, 2015, International Patent Application No. PCT/CN2015/080208 with English translation (5 pages).
Michio, Y. et al. "Study of industrial manufacturing methods for micafungin (FK463)", The Society for Biotechnology, Japan, vol. 83, No. 3, Dec. 31, 2005, pp. 123-131.

*Primary Examiner* — Christina Bradley
(74) *Attorney, Agent, or Firm* — Hamre, Schumann, Mueller & Larson, P.C.

(57) ABSTRACT

Disclosed is a novel polymorph of a cyclic peptide compound, the structure whereof is represented by formula I; also disclosed are a preparation method for same and uses thereof.

I

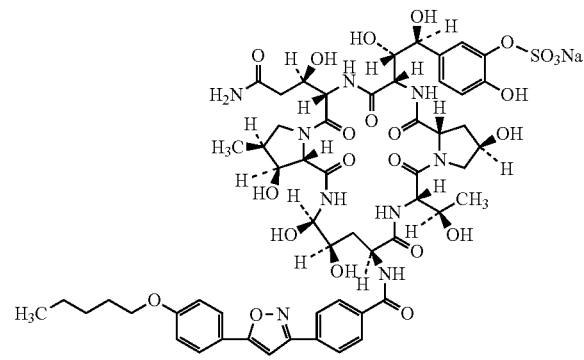

35 Claims, 5 Drawing Sheets

CRYSTAL OF CYCLIC PEPTIDE COMPOUND, PREPARATION METHOD FOR SAME AND USES THEREOF

TECHNICAL FIELD

The present invention relates to novel crystal forms of a compound, and particularly, to novel crystal forms of a cyclic peptide compound as well as the preparation method and use thereof.

BACKGROUND

Micafungin is a novel anti-fungal drug of pneumocandins, and it inhibits the synthesis of a fungi cell wall component, i.e. β-1,3-D-glucan synthase, whereby destroying the structure of fungal cells and thus leading to cytolysis. Micafungin is widely used for treating various infections, such as infections caused by *Aspergillus, Candida, Cryptococcus, Mucor, Actinomyces, Histoplasma, Dermatophytes* and *Fusarium* and the like.

Micafungin Sodium (also named as FK463) is the active pharmaceutical ingredient of the marketed drug, Mycamine. The chemical structure of micafungin Sodium is shown as follows:

formula I

Sodium 5-[(1S,2S)-2-[(3S,6S,9S,11R,15S,18S,20R,21R, 24S,25S,26S)-3-[(R)-2-carbamoyl-1-hydroxyethyl]-11,20, 21,25-tetrahydroxy-15-[(R)-1-hydroxyethyl]-26-methyl-2, 5,8,14,17,23-hexaoxo-18-[4-[5-(4-pentoxyphenyl)isoxazol-3-yl]benzoylamino]-1,4,7,13,16,22-hexaazatricyclo [22.3.0.0$^{9,13}$]heptacosan-6-yl]-1,2-dihydroxyethyl]-2-hydroxy phenyl sulfate.

The compound of formula I is a polypeptide compound with poor stability, and its quality and efficacy are affected by degradation products generated during transportation or long-term storage. Furthermore, the compound of formula I is difficult to be crystallized and generally it is in an amorphous state.

U.S. Pat. Nos. 6,107,458 and 7,199,248 and WO 96/111210 disclosed methods for preparing and purifying the compounds of Formula I. Wherein, in U.S. Pat. No. 7,199,248, Micafungin DIPEA (diisopropylethylamine) salt was purified through filtration and chromatographic separation, and then precipitated with acetone and ethyl acetate to give the amorphous form of the compound of formula I.

Atsushi Ohigashi et at, "Process Development of Micafungin, a Novel Lipopeptide Antifungal Agent", *Journal of Synthesis Organic Chemistry*, 2006, Vol 64 (12), described that the compound of formula I can be precipitated by adding a mixture of acetone and ethyl acetate to the elution solution of the compound of formula I from ion exchange, so as to give the amorphous compound of formula I. Before drying, the content of solvent in the precipitate of the compound of formula I was high (Dry/Wet=0.25), and the precipitate of the compound of formula I contained about 75% of solvent. To effectively remove the solvent, the drying time has to be extended, which, however, will cause an increase in the degradation products of the compound of formula I and a reduction in purity.

All the compounds of formula I obtained by the above prior art methods are in amorphous form. Compared with molecules in a crystalline solid material, molecules in an amorphous solid material possess higher energy, because the orderly and periodic arrangement of molecules will reduce the energy of the interaction between molecules. In accordance with the principles of thermodynamics, high-energy materials have poor stability, while low-energy materials have good stability. In general, the stability of a compound in amorphous state is less than that of the crystal thereof.

In addition, the patent application WO 03/018615 a Fujisawa Pharmaceutical Co., Ltd. disclosed a new crystal form of the compound of the formula I and a preparation method thereof. In WO03/018615, the compound of formula I in amorphous form was dissolved in an aqueous solution of a single alcohol or an aqueous solution of acetone, and a solvent, such as ethyl acetate, methylene chloride, acetone and acetonitrile, was added, so as to give the B82-type acicular crystals of the compound of formula I. The crystal was obtained in an organic solvent, has a needle shape under microscope, and has peaks at the following 2θ angles in the X-ray powder diffraction pattern: 4.6°, 5.5°, 9.0°, 9.8°, 16.9°.

In "Study of Industrial Manufacturing Methods for Micafungin (FK463)", *Seibutsa kogaku Kaishi*, 2005, Vol 83, YAMASHITA, et al., from Fujisawa Pharmaceutical Co., Ltd., mentioned that needle-like crystals of FK463 were successfully obtained through optimization of solvent and control of pH. However, no specific embodiments and crystal data were disclosed. Since the prior patent application WO03/018615 of the company disclosed the B82-type needle-like crystals of the compounds of formula I, it can be seen that what YAMASHITA et al. obtained was also the B82-type needle-like crystal.

The present inventors prepared the B82-type acicular crystal according to the method of Example 1 in WO03/018615, and the resultant crystal was observed with an optical microscope, which reveals that the crystal is about 1 μm in size and has a fine-needle shape. When the crystals were subjected to subsequent processing steps, such as filtration, drying or the like, the present inventors found that, because the B82-type crystals essentially have a fine-needle morphology, it is difficult to filter the crystals of the compound of formula I and the operation needs a long time; before drying of the crystals, the content of solvent in the compound of formula I (Dry/Wet) was about 0.25, and a large amount of organic solvent was trapped in the crystal. To render the content of solvent in compliance with the requirements for active pharmaceutical ingredients (API), the drying temperature or the drying time has to be increased during the drying process. Such drying process, however, will increase the degradation product of the compound of formula I, seriously affecting the quality and stability of API.

At present, the disclosed Micafungin sodium solids are of poor stability and can only be stored at a low temperature or lyophilized with the presence of a large amount of excipients to ensure its stability, which greatly limits the development of pharmaceutical uses of Micafungin sodium. If a stable solid of Micafungin sodium can be found, it can be prepared into various formulations, such as lyophilized powder for injection, tablets, capsules, ointment, etc., to facilitate the use by different patients.

Therefore, there is an urgent need in the art to obtain a new crystalline form of the compound of formula I which is more stable, and easier to be filtered and dried, so that a better commercial production can be achieved.

SUMMARY OF THE PRESENT INVENTION

One object of the present invention is to provide three new crystals of the compound of formula I.

Another object of the present invention is to provide preparation methods of said three new crystals.

Another object of the present invention is to provide uses of said three new crystals.

Crystals of the Compound of Formula I

In the present invention, three new crystals of the compound of formula I are provided.

Crystal A

Crystal A of a cyclic peptide compound, the structure of which is shown in formula I, wherein said crystal A has characteristic peaks at the following 2θ angles in the X-ray power diffraction pattern (XRPD): 3.6±0.2°, 6.4±0.2°, 6.8±0.2°, 9.5±0.2°.

In a preferred embodiment of the present invention, said crystal A further has characteristic peaks at the following 2θ angles in the X-ray power diffraction pattern (XRPD): 7.5±0.2°, 11.0±0.2°, 12.4±0.2°.

In another preferred embodiment of the present invention, said crystal A has additional characteristic peaks at the following 2θ angles in the X-ray power diffraction pattern (XRPD): 13.4±0.2°, 20.2±0.2°.

Figure 1:
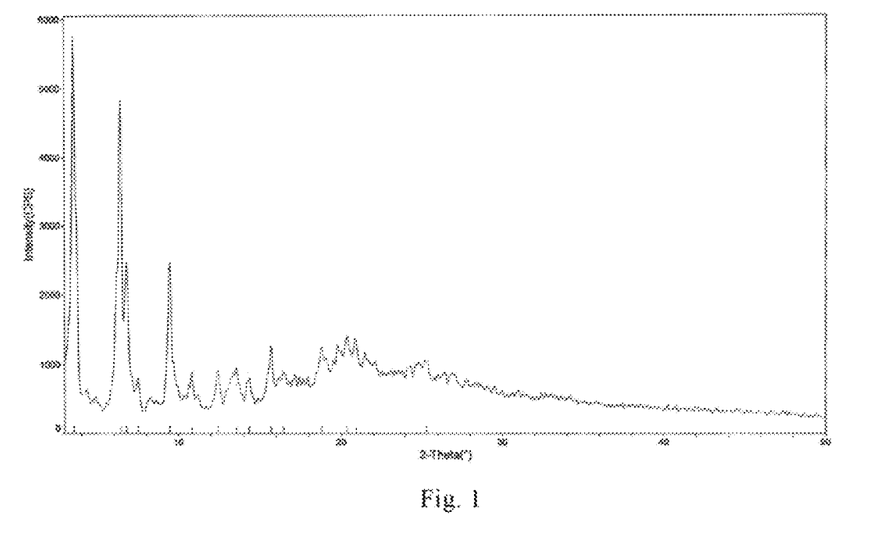

In another preferred embodiment of the present invention, said crystal A of the cyclic peptide compound has the X-ray power diffraction pattern (XRPD) shown in FIG. 1.

Crystal B

Crystal B of a cyclic peptide compound, the structure of which is shown in formula I, wherein said crystal B has characteristic peaks at the following 2θ angles in the X-ray power diffraction pattern (XRPD): 4.4±0.2°, 5.2±0.2°, 8.5±0.2°, 9.6±0.2°.

In another preferred embodiment of the present invention, said crystal B has additional characteristic peaks at the following 2θ angles in the X-ray power diffraction pattern (XRPD): 7.5±0.2°, 8.8±0.2°, 16.6±0.2°, 13.7±0.2°, 22.5±0.2°.

In another preferred embodiment of the present invention, said crystal B has additional characteristic peaks at the following 2θ angles in the X-ray power diffraction pattern (XRPD): 12.6±0.2°, 14.9±0.2°, 15.6±0.2°, 25.1±0.2°.

In another preferred embodiment of the present invention, said crystal B has additional characteristic peaks at the following 2θ angles in the X-ray power diffraction pattern (XRPD): 4.4±0.1°, 5.2±0.1°, 8.5±0.1°, 9.6±0.1°.

In another preferred embodiment of the present invention, said crystal B has additional characteristic peaks at the following 2θ angles in the X-ray power diffraction pattern (XRPD): 7.5±0.1°, 8.8±0.1°, 16.6±0.1°, 13.7±0.1°, 22.5±0.1°.

In another preferred embodiment of the present invention, said crystal B has additional characteristic peaks at the following 2θ angles in the X-ray power diffraction pattern (XRPD): 12.6±0.1°, 14.9±0.1°, 15.6±0.1°, 25.1±0.1°.

Figure 3:
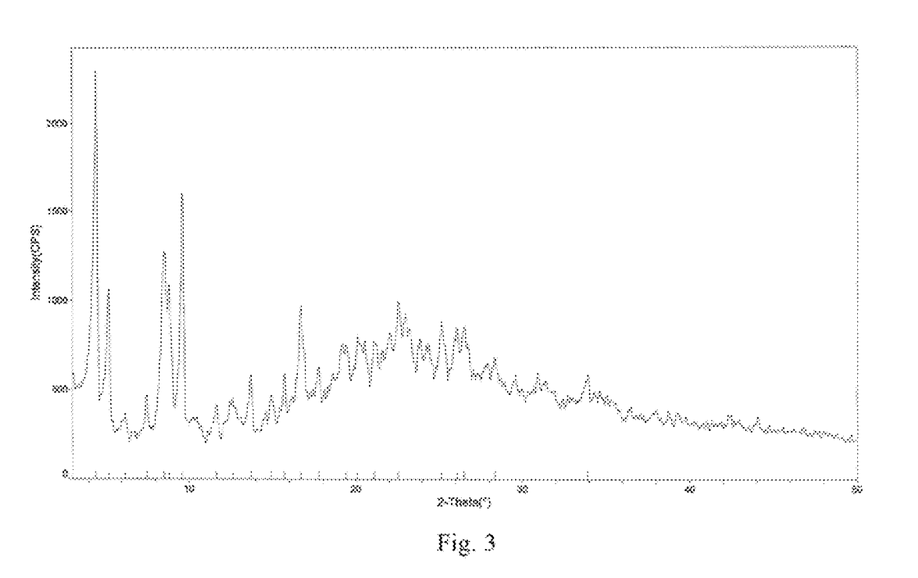

In another preferred embodiment of the present invention, said crystal B of the cyclic peptide compound has the X-ray power diffraction pattern (XRPD) shown in FIG. 3.

Figure 4:
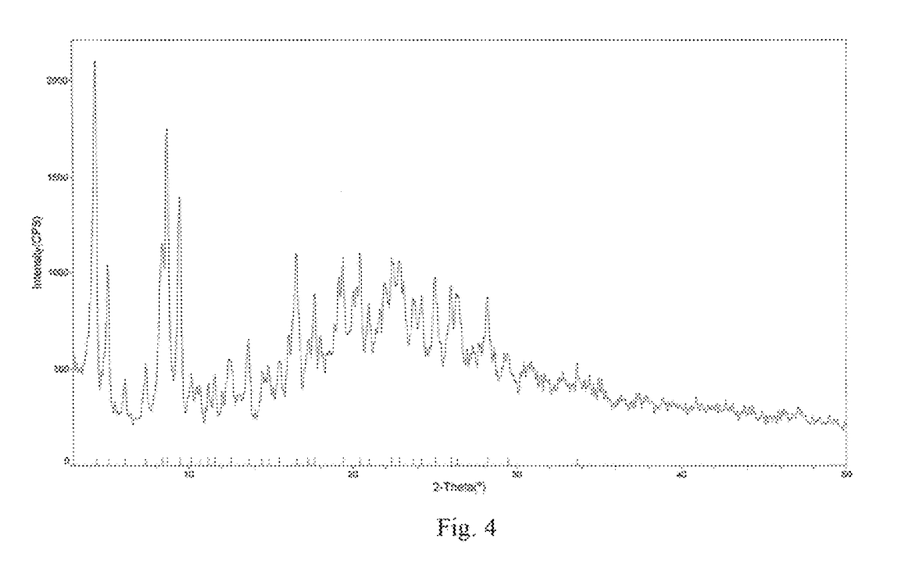

In another preferred embodiment of the present invention, said crystal B of the cyclic peptide compound has the X-ray power diffraction pattern (XRPD) shown in FIG. 4.

Figure 5:
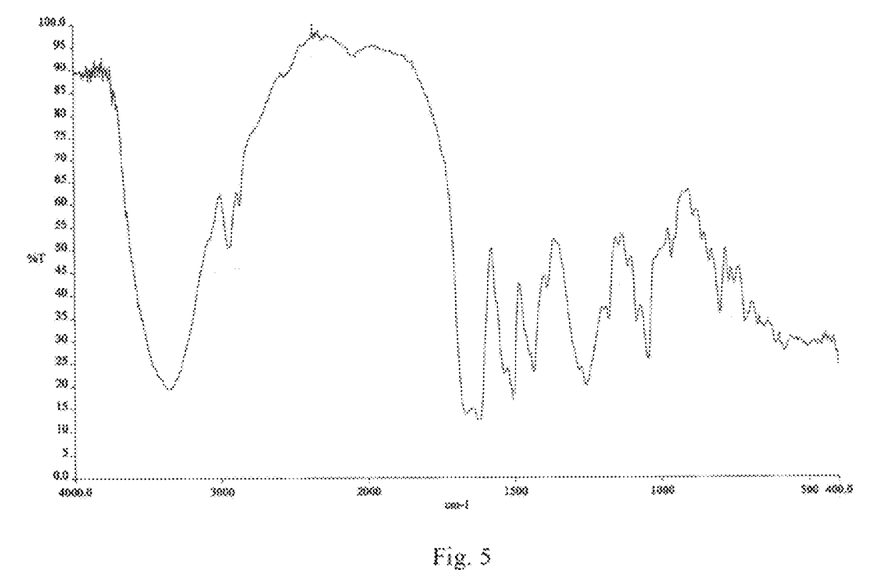
FIG. 5 shows the infrared spectrum (IR) of crystal B of the compound of formula I.

In another preferred embodiment of the present invention, said crystal B of the cyclic peptide compound has the infrared spectrum shown in FIG. 5.

Crystal C

Crystal C of a cyclic peptide compound, the structure of which is shown in formula I, wherein said crystal C has characteristic peaks at the following 2θ angles in the X-ray power diffraction pattern (XRPD): 4.5±0.2°, 5.3±0.2°, 8.6±0.2°, 9.6±0.2°.

Figure 6:
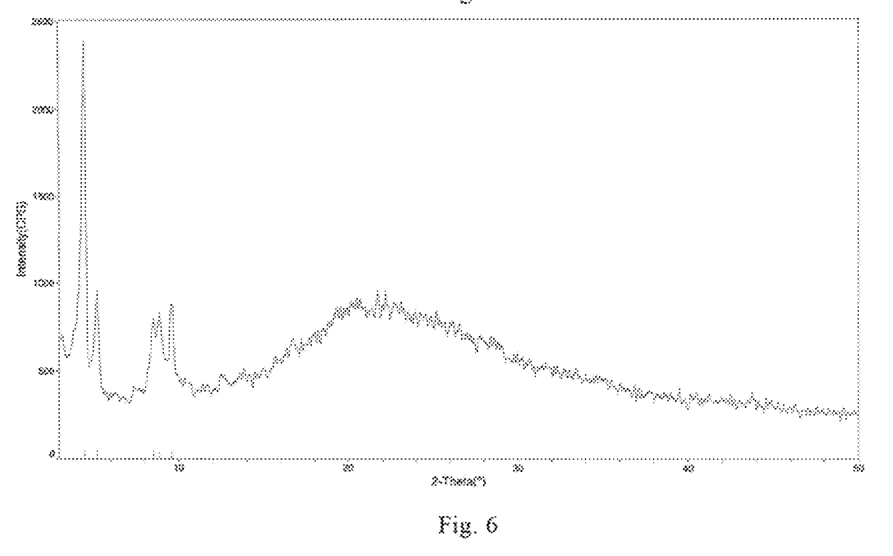

In another preferred embodiment of the present invention, said crystal C of the cyclic peptide compound has the X-ray power diffraction pattern (XRPD) shown in FIG. 6.

Needle-like crystals of B82 type disclosed in WO03/018615 are in a form of fine needle. The crystals are difficult to be filtered or dried, and they also have poor stability. In order to obtain a new crystal of the compound of formula I with better stability and better morphology, the present inventors have studied the solvent system for the crystallization of the compound of formula I. Through the study, the inventors found that: if only biphasic system, such as methanol/water, ethanol/water, n-propanol/water, isopropanol/water, isobutyl alcohol/water, n-butanol/water, acetonitrile/water, acetone/water, is used as the crystallization solvent for the compound of formula I, and the compound of formula I is precipitated by cooling and/or addition of an organic solvent, the precipitated solids are all in amorphous form and of very poor stability upon X-ray powder diffraction (XRPD) analysis. In further studies, we have made enormous adjustments to the ratio of water and the pH value for crystallization in the above biphasic systems. There were totally 236 different combinations of solvent systems, but it was found that all the obtained products were in amorphous form.

The inventors did not abandon their efforts and they continued to use different solvent combinations in a three-phase system to screen for crystallization solvent systems. Upon a long period of research, the present inventors have unexpectedly found that column-like crystals with regular morphology can be obtained in a specific three-phase solvent system. Afterwards, a large number of solvent screening tests were carried out. Three crystals of the compound of formula I, namely, crystal A, crystal B and crystal C, which have better stability and better morphology, were finally obtained, and the preparation processes were established. Compared with the needle-like crystals of B82 type disclosed in WO03/018615, crystal A of the present invention is column-like, large in crystal particle and easy to be filtered; the solvent in the crystal can also be easily removed, and more importantly, the stability of crystal A is significantly superior than that of the crystal of B82 type. Crystal B and C are formed through the removal of organic solvent in crystal A. As determined by gas chromatography, residual contents of the organic solvent in crystals B and C were in compliance with the standard of ICH-Q3C (International Council for Harmonisation of Technical Requirements for Registration of Pharmaceuticals for Human Use, abbreviated as ICH) and with the requirements for residual solvent limits of API. The B82-type crystal, nevertheless, is obtained by filtration without being subjected to the processing steps such as drying and removal of organic solvents. The content of residual solvent is higher than 50%, which is far beyond the limit of solvent residue stipulated in ICH-Q3C and can not meet the requirement of API. Therefore, crystal B and crystal C of the present invention are by far superior to the crystal of B82 type in the amount of residual solvent.

Identification and Properties of the Crystals of the Compound of Formula I

After obtaining the crystals of the compound of formula I, the present inventors have further studied properties of the crystals by using various means and instruments.

At present, X-ray powder diffraction, also called X-ray polycrystal diffraction (XRD or XRPD), is commonly used as the test method for determining the structure of crystal (i.e., crystal form). X-ray powder diffractometer is used, and a series of diffraction patterns are produced when X-ray passes through a crystal. In the pattern, different diffraction lines and the intensities thereof are determined by atomic clusters having certain structure, thereby determining the structure of a crystal. The methods for determining the X-ray power diffraction pattern of a crystal are already known in the art. For example, X-ray power diffraction pattern can be obtained by using the RIGAKU D/max 2550VB/PC X-ray powder diffractometer with a scanning rate of 2°/min and a copper radiation target.

Crystal A of the compound of formula I according to the present invention has a unique crystal morphology, and there are specific characteristic peaks in the X-ray diffraction pattern. Particularly, crystal A of the compound of formula I according to the present invention possesses characteristic peaks at the following 2θ angles in the X-ray powder diffraction pattern: 3.6±0.2°, 6.4±0.2°, 6.8±0.2°, 9.5±0.2°; in a preferred embodiment, there are additional characteristic peaks at the following 2θ angles in the pattern: 7.5±0.2°, 11±0.2°, 12.4±0.2°; and in another preferred embodiment, there are additional characteristic peaks at the following 2θ angles in the pattern: 13.4±0.2°, 20.2±0.2°. More preferably, the crystal A of the compound of formula has an X-ray power diffraction pattern (XRPD) that is substantially identical with FIG. 1.

Crystal B of the compound of formula I according to the present invention has a unique crystal morphology, and there are specific characteristic peaks in the X-ray diffraction pattern. Particularly, crystal B of the compound of formula according to die present invention possesses characteristic peaks at the following 2θ angles in the X-ray powder diffraction pattern: 4.4±0.2°, 5.2±0.2°, 8.5±0.2°, 9.6±0.2°; in a preferred embodiment, there are additional characteristic peaks at the following 2θ angles in the pattern: 7.5±0.2°, 8.8±0.2°, 16.6±0.2°, 13.7±0.2°, 22.5±0.2°; and in another preferred embodiment, there are additional characteristic peaks at the following 2θ angles in the pattern: 12.6±0.2°, 14.9±0.2°, 15.6±0.2°, 25.1±0.2°. In a preferred embodiment, crystal B of the compound of formula I according to the present invention possesses characteristic peaks at the following 2θ angles in the X-ray powder diffraction pattern: 4.4±0.1°, 5.2±0.1°, 8.5±0.1°, 9.6±0.1°; in another preferred embodiment, there are additional characteristic peaks at the following 2θ angles in the pattern: 7.5±0.1°, 8.8±0.1°, 16.6±0.1°, 13.7±0.1°, 22.5±0.1°; and in another preferred embodiment, there are additional characteristic peaks at the following 2θ angles in the pattern: 12.6±0.1°, 14.9±0.1°, 15.6±0.1°, 25.1±0.1°. More preferably, the crystal B of the compound of formula I has an X-ray power diffraction pattern (XRPD) that is substantially identical with FIG. 3 or 4.

For the X-ray powder diffraction method, the state of a substance is identified by comparing the relative intensity of diffraction peaks and the value of mirror spacing distance d (or 2θ) between drug samples of different crystal forms. Regarding the deviation of 2θ angle for a crystal form, it is stipulated in Japanese Pharmacopoeia that: "for different crystalline forms of the same chemical drug, the allowable deviation of 2θ should be less than ±0.2°." Relevant provisions also can be found in US Pharmacopoeia (USP27, Page 2401-2402): "The diffraction angles of the sample and the reference should be consistent within the accuracy range of the diffractometer calibration (2θ value should be reproducible, ±0.10°)". Therefore, for two crystals of the same compound, when the deviation of characteristic peaks on the X-ray powder diffraction pattern is greater than ±0.2°, the characteristic peaks will be considered as being different, and the two crystals are of different crystal forms.

The peaks at the 2θ reflection angle on the X-ray powder diffraction pattern of crystal B of the compound of formula I according to the present invention are specific characteristic peaks, which are significantly different from the characteristic peaks at the 2θ reflection angle on the X-ray powder diffraction pattern of the B82-type crystal disclosed in WO03/018615. Absorption intensities and 2θ angles of crystal B of the compound of formula I and the B82-type crystal are compared as follows: (1) for crystal B prepared in the present invention, there is a characteristic absorption peak of moderate intensity at 5.1-5.2°, while in X-ray powder diffraction pattern of the B82-type crystal disclosed in WO03/018615, there is only an absorption peak at 5.5°, the two characteristic peaks differing by 0.3-0.4°. According to the requirements in Japanese Pharmacopoeia and US Pharmacopoeia, and considering the fact that the error range of the existing X-ray powder diffractometers is generally within 0.1° and up to 0.2° at the most, the difference between the two characteristic peaks is not caused by instrument error, but instead, the two peaks are indeed different characteristic peaks; (2) for crystal B prepared in the present invention, there is a characteristic absorption peak of moderate intensity at 8.4-8.5°, while in the X-ray powder diffraction pattern of the B82-type crystal disclosed in WO03/018615, there is only an absorption peak at 9.0°, the two characteristic peaks differing by 0.5-0.6°. According to the requirements in Japanese Pharmacopoeia and US Pharmacopoeia, and considering the fact that the error range of the existing X-ray powder diffractometers is generally within 0.1° and up to 0.2° at the most, the difference between the two characteristic peaks is not caused by instrument error, but instead, the two peaks are indeed different characteristic peaks; (3) for crystal B of the present invention, the strongest characteristic absorption peak is at 4.4°, while for the crystal of B82 type, the strongest absorption peak is at 9.8°. Therefore, X-ray powder diffraction patterns of crystal B of the compound of formula I prepared in the present invention and the crystal of B82 type are different, and the crystals are of different crystal forms.

Crystal C of the compound of formula I according to the present invention has a unique crystal morphology, and there are specific characteristic peaks in the X-ray diffraction pattern. Particularly, crystal C of the compound of formula I according to the present invention possesses characteristic peaks at the following 2θ angles in the X-ray powder diffraction pattern: 4.5±0.2°, 5.3±0.2°, 8.6±0.2°, 9.6±0.2°. More preferably, crystal C of the compound of formula I has an X-ray power diffraction pattern (XRPD) that is substantially identical with FIG. 6.

The crystal structure is qualitatively determined by Infrared Spectrometry (IR) which is known in the art. For example, it can be determined by using PE Spectrum One B, tableting at KBr: sample=200:1, and scanning 400-4000 $cm^{-1}$.

In the IR pattern of crystal B of the compound of formula I according to the present invention, there are characteristic peaks at the following wave numbers: 3340.16 $cm^{-1}$, 2954.82 $cm^{-1}$, 1625.74 $cm^{-1}$, 1505.84 $cm^{-1}$, 1436.10 $cm^{-1}$, 1255.82 $cm^{-1}$, 1178.41 $cm^{-1}$, 1085.09 $cm^{-1}$, 1046.10 $cm^{-1}$, 965.79 $cm^{-1}$, 838.03 $cm^{-1}$, 802.51 $cm^{-1}$, 770.45 $cm^{-1}$, 752.44 $cm^{-1}$, 715.64 $cm^{-1}$, 612.14 $cm^{-1}$. More preferably, the IR pattern is substantially identical with FIG. 5.

Characteristic peaks on the infrared spectrum of crystal B of the compound of formula I according to the present invention are particular characteristics, and the infrared spectrum of crystal B of the compound of formula I is significantly different from that of the B82-type crystal disclosed in WO03/018615 which has characteristic peaks at the wave number of 1050 $cm^{-1}$ to 900 $cm^{-1}$.

Micro-analysis technology serves the purpose of analyzing crystal forms through identification of the exterior shape of a crystal by using an optical microscope. Under an optical microscope, crystal A of the compound of formula I according to the present invention is a column-like crystal, while the crystal of B82 type is a fine needle-like crystal.

The content of water in the compound of formula I is determined by assays commonly known in the art. For example, the water content is determined by Karl Fischer (KF).

High performance liquid chromatography (HPLC) is a common method for determining the purity of a compound, wherein a liquid is used as the mobile phase and a high-pressure transfusion system is used for pumping the mobile phase, such as single solvents with different polarities, a mixture of solvents at different proportions, or buffers, into a column packed with a stationary phase. Each component is separated in the column, and then enters into a detector for detection, thereby analyzing a sample. In the present invention, HPLC is used for determining the purity of the compound of formula I and studying the stability of a sample. The HPLC method is as follows:

Analysis Column: YMC-ODS 250×4.6 mm, 5 μm;
Mobile phase: acetonitrile:phosphate buffer (pH 3.0)=45:70;
Flow rate: 1 ml/min;
Column temperature: 35° C.;
Diluent: aqueous phosphate buffer;
Detection wavelength: 210 nm;
Injection volume: 10 μl.

Preparation of Crystals of the Compound of Formula I

The present invention provides a method for preparing crystals of the compound of formula I.

During the course of study, the inventors have not only screened solvents for crystallization, but also studied the effect of pH on the crystal of the compound of formula I by changing the pH value during crystallization. Extensive experimentation has shown that pH is not a decisive factor in obtaining crystals of the compound of formula I. When a two-phase or three-phase solvent system is used for crystallization which produces the compound of formula I in amorphous form, it yields solids in amorphous form even when the pH is changed. However, after crystal A is obtained by using a three-phase solvent system in crystallization, even when the pH is changed, crystal A can still be obtained, as long as the compound of formula I is stable.

The inventors have established the following preparation methods for obtaining the three new crystals of the compound of formula I.

A preparation method for crystal A of the cyclic peptide compound, which comprises the steps of:
(a) dissolving the compound of formula I in an aqueous mixed solution of alcohols;
(b) obtaining said crystal A of the cyclic peptide compound by reducing the temperature and/or adding an organic solvent (i).

Wherein the mixed solution of alcohols in step (a) is selected from a group consisting of methanol/isobutanol, methanol/isopropanol, and methanol/n-propanol.

Wherein, in the aqueous mixed solution of alcohols in step (a), the volume ratio of the two alcohols is 0.01-100, preferably 0.05-20, and more preferably 0.1-10.

Wherein, in the aqueous mixed solution of alcohols in step (a), the ratio of the total volume of the alcohol to the volume of water is 0.1 to 100, preferably 0.5 to 10, and more preferably 1 to 7.

Wherein, the temperature of dissolving in step (a) is 10-50° C., preferably, 20-40° C.

Wherein, in step (a), there is 1-500 mg/ml, preferably 5-100 mg/ml, more preferably 10-50 mg/ml of the compound of formula I, based on the total volume of the solution.

Wherein, in step (b), the organic solvent (i) is selected from a group consisting of n-propanol, isopropanol, isobutanol, methyl acetate, ethyl acetate, n-propyl acetate, isopropyl acetate.

Wherein, in step (b), the temperature is reduced to −40 to 35° C., preferably −20 to 35° C., more preferably −10 to 30° C., most preferably −5 to 15° C.

Wherein the volume ratio of the organic solvent (i) in step (b) to the aqueous mixed solution of alcohols in step (a) is 0.1 to 50, preferably 0.1 to 10, and more preferably 1-5.

A preparation method for crystal B of the cyclic peptide compound, which comprises the step of:
vacuum-drying crystal A of the cyclic peptide compound together with a water system and controlling the content of water, thereby obtaining crystal B of the cyclic peptide compound.

Wherein the water system is selected from a group consisting of tap water, pure water, ice-water mixture and other substance capable of releasing water vapor.

wherein, "vacuum-drying crystal A of the cyclic peptide compound together with a water system" means that crystal A of the cyclic peptide compound is situated in a place where a sample is generally put in a vacuum-dryer, and an open container containing a substance capable of releasing water vapor is arranged in the vicinity of the crystal A of the cyclic peptide compound.

Wherein the content of water is controlled at 4%-22%.

A preparation method for crystal C of the cyclic peptide compound, which comprises the step of:
vacuum-drying crystal B of the cyclic peptide compound and controlling the content of water, thereby obtaining crystal C of the cyclic peptide compound.

Wherein the content of water is controlled at less than 4%.

Wherein "vacuum drying" is a conventional method in the art, for example, but not limited to, drying using a vacuum drying oven.

Uses of the Crystals of the Compound of Formula I and the Composition Thereof

The crystals of the compound of formula I provided in the present invention also can be directly used in the preparation of medicaments for treating fungal infections. A pharmaceutical composition comprising a crystal of the compound of formula I and a pharmaceutically acceptable carrier can also be provided.

Relevant Terms

As used herein, the term "crystal" means the solid of a molecule or atom complex showing specific arrangement.

As used herein, "the compound of formula I", "compound I" and "the compound according to formula I" can be interchangeably used, all of which mean an amorphous substance with the structure of formula I or a substance of a crystal form other than the crystals A-C of the compound of formula I according to the present invention, and all of which refer to a compound of the following structural formula:

formula I

The compound of formula I can be obtained by routine methods in the art, for example (but not limited to), the preparation method disclosed in WO96/11210; or alternatively, the compound can be commercially obtained, such as from Fujisawa, Japan.

As used herein, the term "pharmaceutically acceptable carrier" refers to the carriers that can be used in the administration of therapeutics, including various excipients and diluents. This term refers to the drug carriers which themselves are not necessary active ingredients, and will not produce undue toxicity upon administration. Suitable carriers are generally known to the skilled in the art. Detailed review regarding pharmaceutical acceptable excipients can be found in Remington's Pharmaceutical Sciences (Mack Pub, Co., N.J. 1991). Pharmaceutically acceptable excipients in a composition may include liquid, such as water, saline, glycol and ethanol. Additionally, auxiliary substances, such as disintegrating agents, wetting agents, emulsifying agents, pH buffering substances, etc., can be present in the carriers.

The advantages of the invention mainly include:

1. Providing three crystal forms of the compound of formula I, which crystals are of regular morphology and superior stability, and convenient for transportation and storage, thereby resolving the technical problems that need to be urgently addressed in the art.

2. Providing methods for preparing the crystal forms of the compound of formula I, which methods are highly suitable for large-scale production and have a high yield.

BRIEF DESCRIPTION OF THE DRAWINGS

FIG. 1 shows the X-ray powder diffraction (XRPD) pattern of crystal A of the compound of formula I; wherein

| Number of peak | 2 θ | d(A) | I % (Relative Intensity) |
| --- | --- | --- | --- |
| 1 | 3.6 | 24.7974 | 100.0 |
| 2 | 6.4 | 13.7127 | 84.0 |
| 3 | 6.8 | 12.9885 | 42.9 |
| 4 | 7.5 | 11.7774 | 14.0 |
| 5 | 9.4 | 9.3605 | 42.8 |
| 6 | 10.8 | 8.1551 | 15.5 |
| 7 | 12.4 | 7.1206 | 15.8 |
| 8 | 13.6 | 6.5156 | 16.7 |
| 9 | 20.4 | 4.3580 | 24.6 |

FIG. 3 shows the X-ray powder diffraction (XRPD) pattern of crystal B of the compound of formula I, wherein

| Number of peak | 2 θ | d(A) | I % (Relative Intensity) |
| --- | --- | --- | --- |
| 1 | 4.4 | 19.8888 | 100.0 |
| 2 | 5.2 | 17.0426 | 46.0 |
| 3 | 7.5 | 11.8100 | 20.3 |
| 4 | 8.5 | 10.3938 | 55.2 |
| 5 | 8.8 | 10.0411 | 46.5 |
| 6 | 9.6 | 9.2244 | 69.7 |
| 7 | 12.6 | 7.0200 | 19.3 |
| 8 | 13.7 | 6.4581 | 25.4 |
| 9 | 14.9 | 5.9329 | 20.4 |
| 10 | 15.7 | 5.6400 | 25.4 |
| 11 | 16.7 | 5.3169 | 41.9 |
| 12 | 22.5 | 3.9443 | 43.0 |
| 13 | 25.1 | 3.5395 | 38.0 |

FIG. 4 shows the X-ray powder diffraction (XRPD) pattern of crystal B of the compound of formula I; wherein

| Number of peak | 2 θ | d(A) | I % (Relative Intensity) |
| --- | --- | --- | --- |
| 1 | 4.4 | 20.1588 | 100.0 |
| 2 | 5.1 | 17.2445 | 49.4 |
| 3 | 7.4 | 11.9038 | 24.8 |
| 4 | 8.4 | 10.5159 | 54.1 |
| 5 | 8.7 | 10.1314 | 83.6 |
| 6 | 9.5 | 9.3212 | 66.8 |
| 7 | 12.6 | 7.0423 | 25.9 |
| 8 | 13.6 | 6.4868 | 31.3 |
| 9 | 14.8 | 5.9638 | 24.6 |
| 10 | 15.5 | 5.7043 | 26.0 |
| 11 | 16.6 | 5.3426 | 52.3 |
| 12 | 22.4 | 3.9724 | 51.0 |
| 13 | 25.0 | 3.5535 | 46.1 |

FIG. 6 shows the X-ray powder diffraction (XRPD) pattern of crystal C of the compound of formula I; wherein

| Number of peak | 2 θ | d(A) | I % (Relative Intensity) |
| --- | --- | --- | --- |
| 1 | 4.5 | 19.7047 | 100.0 |
| 2 | 5.2 | 16.8487 | 40.0 |
| 3 | 8.5 | 10.3453 | 33.1 |
| 4 | 9.6 | 9.2051 | 37.3 |

MODE FOR CARRYING OUT THE INVENTION

The invention will be further illustrated with reference to the following specific examples. It is to be understood that these examples are only intended to illustrate the invention, but not to limit the scope of the invention. In the following examples, the experimental methods without articulating specific experimental conditions are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

In the following Comparative Examples and Examples, residual solvent in the crystal was determined by GC (Gas Chromatography) according to the second method in Appendix VIIIP of Part II of Chinese Pharmacopoeia (2010 edition), wherein the column used was a capillary chromatography column with polyethylene glycol as stationary phase; the initial temperature was 40° C. for 5 min, raised to 60° C. at 5° C./min, and further raised to 240° C. at 30° C./min for 3 min; the temperature at the inlet was 200° C.; the temperature at the detector was 260° C.; the equilibrium temperature of headspace bottle was 120° C.; and the equilibrium time was 20 min.

Comparative Example 1

Preparation of the Crystal of B82 Type
Needle-like crystals, i.e., crystals of B82 type, were obtained according to the method of Example 1 of WO03/018615. The total amount of residual solvent in the crystal of B82 type was determined as 72.8% (mass percentage) by GC (Gas Chromatography).

Example 1

Figure 7:
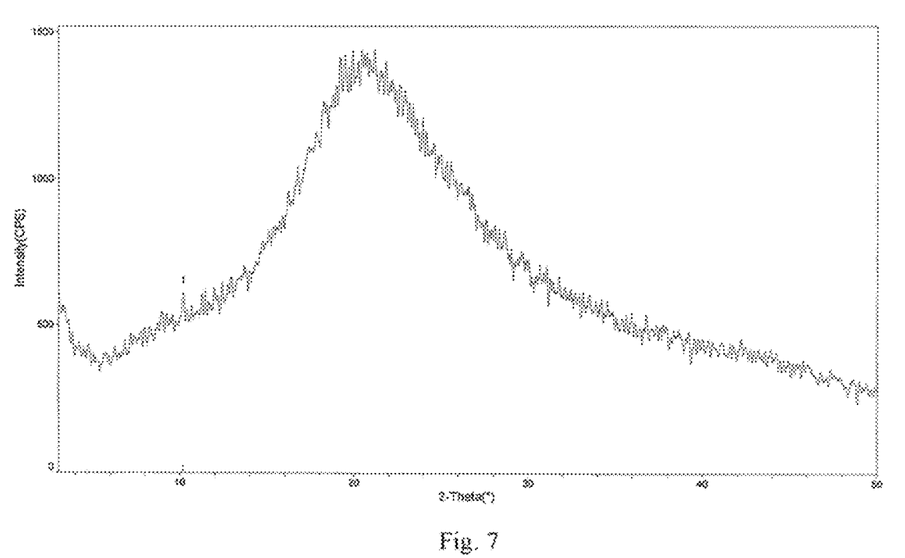
FIG. 7 shows the X-ray powder diffraction (XRPD) pattern of the compound of formula I in amorphous form.
Figure 8:
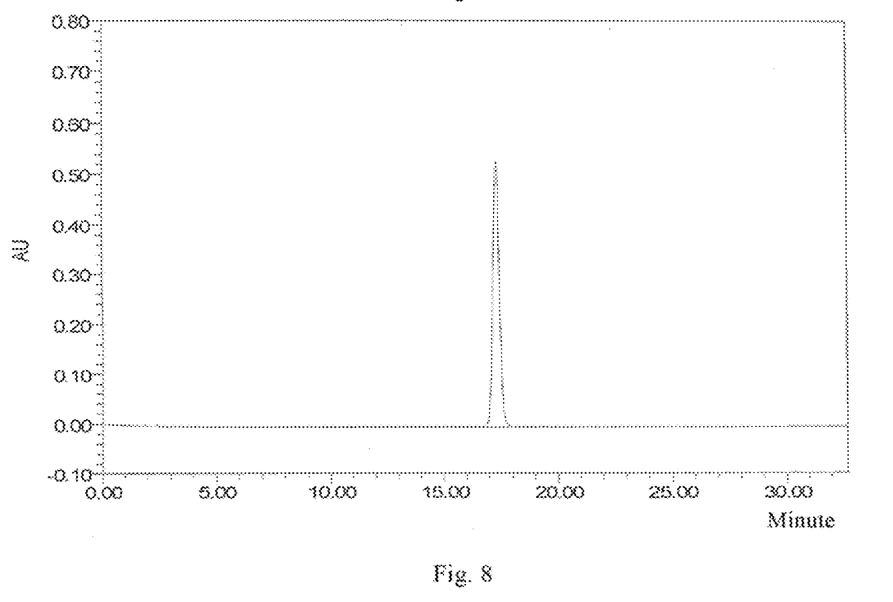
FIG. 8 is a HPLC pattern for crystal B of the compound of formula I obtained in Example 11 after being placed at 25° C. for 30 days.
Figure 9:
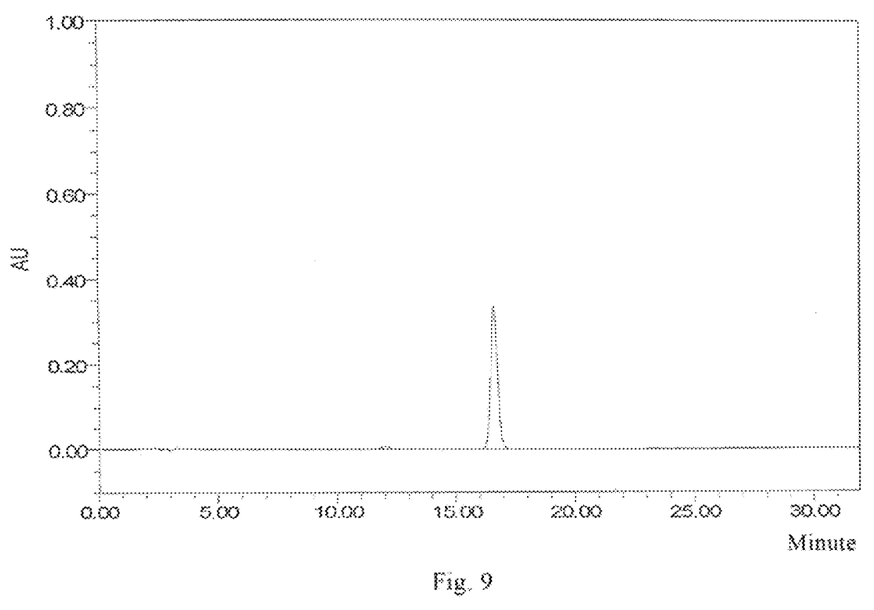
FIG. 9 is a HPLC pattern for the B82-type crystal obtained in Comparative Example 1 after being placed at 25° C. for 30 days.

Preparation of Compound I
The solid amorphous powder of the compound of formula I was prepared according to the method of U.S. Pat. No. 7,199,248, and the X-ray powder diffraction pattern thereof is shown in FIG. 7.

Example 2

Preparation of Crystal A of the Compound of Formula I
At 25° C., 1 g of the compound of formula I in amorphous form prepared in Example 1 was dissolved into 50 ml of an aqueous methanol/isobutanol solution (isobutanol:water:methanol=8:2:1). The resultant solution was slowly cooled to 8° C., crystals precipitated from the solution. The system was stirred for 3.5 hours at this temperature, so that a large amount of crystals precipitated. 90 ml of ethyl acetate were slowly added, and the crystals were sampled before filtration and observed under a microscope (15×40), photograph of which can be found in FIG. 2. Crystal A was obtained by filtration, and the XRPD pattern thereof can be found in FIG. 1. The total amount of residual solvent in crystal A was determined as 30.2% (mass percentage) by GC (Gas Chromatography).

Example 3

Preparation of Crystal A of the Compound of Formula I
At 30° C., 2.5 g of the crystals of B82 type prepared in Comparative Example 1 were dissolved into 50 ml of an aqueous methanol/isobutanol solution (isobutanol:water:methanol=1:1:1), 50 ml of methyl acetate were slowly added, and crystal A was obtained by filtration. The total amount of residual solvent in crystal A was determined as 28.4% (mass percentage) by GC (Gas Chromatography).

Example 4

Preparation of Crystal A of the Compound of Formula I
At 10° C., 3 g of the compound of formula I in amorphous form prepared in Example 1 were dissolved into 600 ml of an aqueous methanol/isobutanol solution (isobutanol:water:methanol=5:1:2), the resultant solution was cooled to −20° C., crystals precipitated from the solution, and the system was stirred for 12 hours, so that a large amount of crystals precipitated. Crystal A was obtained by filtration, and the total amount of residual solvent in crystal A was determined as 25.1% (mass percentage) by GC (Gas Chromatography).

Example 5

Preparation of Crystal A of the Compound of Formula I
At 50° C., 3 g of the compound of formula I in amorphous form prepared in Example 1 were dissolved into 1.20 ml of an aqueous methanol/isopropanol solution (isopropanol:water:methanol=1:4:1), the resultant solution was cooled to 30° C., crystals precipitated from the solution, and the system was stirred for 30 mins, so that a large amount of crystals precipitated. 200 ml of isopropanol were slowly added, and crystal A was obtained by filtration. The total amount of residual solvent in crystal A was determined as 27.1% (mass percentage) by GC (Gas Chromatography).

Example 6

Preparation of Crystal A of the Compound of Formula I
At 20° C. 1 g of the compound of formula I in amorphous form prepared in Example 1 was dissolved into 20 ml of an aqueous methanol/isopropanol solution (isopropanol:water:methanol=10:2:1), 200 ml of n-propyl acetate were slowly added, and crystal A was obtained by filtration. The total amount of residual solvent in crystal A was determined as 26.9% (mass percentage) by GC (Gas Chromatography).

Example 7

Preparation of Crystal A of the Compound of Formula I
At 18° C., 1.0 g of the compound of formula in amorphous form prepared in Example 1 was dissolved into 100 ml of an aqueous methanol isopropanol solution (isopropanol:water:methanol=1:2:20), the resultant solution was cooled to −5° C., crystals precipitated from the solution, and the system was stirred for 4 hours, so that a large amount of crystals precipitated. Crystal A was obtained by filtration, and the total amount of residual solvent in crystal A was determined as 33.4% (mass percentage) by GC (Gas Chromatography).

Example 8

Preparation of Crystal A of the Compound of Formula I

At 30° C., 2 g of the compound of formula I in amorphous form prepared in Example 1 were dissolved into 20 ml of an aqueous methanol/n-propanol solution (n-propanol:water:methanol=1:15:10), the resultant solution was cooled to 15° C., crystals precipitated from the solution, and the system was stirred for 2 hours, so that a large amount of crystals precipitated. 100 ml of isopropyl acetate were slowly added, and crystal A was obtained by filtration. The total amount of residual solvent in crystal A was determined as 32.0% (mass percentage) by GC (Gas Chromatography).

Example 9

Preparation of Crystal A of the Compound of Formula I

At 25° C., 4 of the compound of formula I in amorphous form prepared in Example 1 were dissolved into 300 ml of an aqueous methanol/n-propanol solution (n-propanol:water:methanol=20:2:1), 30 ml of isobutanol were slowly added, and crystal A was obtained by filtration. The total amount of residual solvent in crystal A was determined as 35.1% (mass percentage) by GC (Gas Chromatography).

Example 10

Preparation of Crystal A of the Compound of Formula I

At 40° C., 2.7 g of the compound of formula I in amorphous form prepared in Example 1 were dissolved into 80 ml of an aqueous methanol/n-propanol solution (n-propanol:water:methanol=10:3:1), the resultant solution was cooled to −10° C., crystals precipitated from the solution, and the system was stirred for 1 hour, so that a large amount of crystals precipitated. Crystal A was obtained by filtration. The total amount of residual solvent in crystal A was determined as 30.0% (mass percentage) by GC (Gas Chromatography).

Example 11

Preparation of Crystal B of the Compound of Formula I

At 20° C., 1.5 g of the compound of formula I in amorphous form prepared in Example 1 were dissolved into 70 ml of an aqueous methanol/isobutanol solution (isobutanol:water:methanol=8:2:1), the resultant solution was cooled to 0° C., crystals precipitated from the solution, and the system was stirred for 4.5 hours, so that a large amount of crystals precipitated. 100 ml of ethyl acetate were slowly added, and crystal A was obtained by filtration. The obtained crystals were placed into a vacuum-dryer, and a plate of pure water was put on the bottom of the vacuum-dryer. The content of water was controlled at 17.9%, and crystal B was obtained by vacuum-drying. The XRPD pattern and IR spectrum of crystal B are shown in FIGS. 3 and 5. The total amount of residual solvent in crystal A was determined as 0.8% (mass percentage) by GC (Gas Chromatography).

Example 12

Preparation of Crystal B of the Compound of Formula I

At 35° C., 2.3 g of the compound of formula I in amorphous form prepared in Example 1 were dissolved into 100 ml of an aqueous ethanol/n-propanol solution (n-propanol:water:methanol=6:2:1), the resultant solution was cooled to 10° C. crystals precipitated from the solution, and the system was stirred for 3 hours at this temperature, so that a large amount of crystals precipitated. 100 ml of ethyl acetate were slowly added, and crystal A was obtained by filtration. The obtained crystals were placed into a vacuum-dryer, and a plate of ice-water mixture was put on the bottom of the vacuum-dryer. The content of water was controlled at 22%, and crystal B was obtained by vacuum-drying. The total amount of residual solvent in crystal A was determined as 0.6% (mass percentage) by GC (Gas Chromatography).

Example 13

Preparation of Crystal B of the Compound of Formula I

The crystals obtained in Example 2 were placed into a vacuum-dryer, and a plate of tap water was put on the bottom of the vacuum-dryer. The content of water was controlled at 12.1%, and crystal B was obtained by vacuum-drying. The XRPD pattern of crystal B are shown in FIG. 4. The total amount of residual solvent in crystal A was determined as 0.7% (mass percentage) by GC (Gas Chromatography).

Example 14

Preparation of Crystal B of the Compound of Formula I

The crystals obtained in Example 6 were placed into a vacuum-dryer, and a plate of crushed ice was put on the bottom of the vacuum-dryer. The content of water was controlled at 4%, and crystal B was obtained by vacuum-drying. The total amount of residual solvent in crystal A was determined as 0.8% (mass percentage) by GC (Gas Chromatoaraphy).

Example 15

Preparation of Crystal C of the Compound of Formula I

At 27° C., 2 g of the compound of formula I in amorphous form prepared in Example 1 were dissolved into 100 ml of an aqueous methanol/isobutanol solution (isobutanol:water:methanol=8:2:1), the resultant solution was slowly cooled to 0° C., crystals precipitated from the solution, and the system was stirred for 4 hours at this temperature, so that a large amount of crystals precipitated. 150 ml of ethyl acetate were slowly added, and crystal A was obtained by filtration. The obtained crystals were placed into a vacuum-dryer, and a plate of tap water was put on the bottom of the vacuum-dryer. The content of water was controlled at 17.7%, and crystal B was obtained by vacuum-drying. The plate of tap water was then removed, and the sample was further dried. When the content of water was determined as 2.1%, crystal C of the compound of formula I was obtained. The XRPD pattern of crystal C is shown in FIG. 6. The total amount of residual solvent in crystal A was determined as 0.5% (mass percentage) by GC (Gas Chromatography).

Example 16

Preparation of Crystal C of the Compound of Formula I

At 20° C., 3.3 g of the compound of formula I in amorphous form prepared in Example 1 were dissolved into 120 ml of an aqueous methanol/isopropanol solution (isopropanol:water:methanol=3:1:3), the resultant solution was cooled to 5° C., crystals precipitated from the solution, and the system was stirred for 1.5 hours at this temperature, so that a large amount of crystals precipitated. 200 ml of n-propyl acetate was slowly added, and crystal A was obtained by filtration. The obtained crystals were placed into a vacuum-dryer, and a plate of pure water was put on the bottom of the vacuum-dryer. The content of water was controlled at 7.6%, and crystal B of the compound of formula I was obtained by vacuum-drying. The plate of pure water was then removed, and the sample was further vacuum-dried. When the content of water was determined as 3.7%, crystal C of the compound of formula I was obtained. The total amount of residual solvent in crystal A was determined as 0.5% (mass percentage) by GC (Gas Chromatography).

Example 17

Preparation of Crystal C of the Compound of Formula I

Crystal B obtained in Example 13 was vacuum-dried. When the content of water was determined as 2.9%, crystal C was obtained. The total amount of residual solvent in crystal A was determined as 0.4% (mass percentage) by GC (Gas Chromatography).

Example 18

Preparation of Crystal C of the Compound of Formula I

Crystal B obtained in Example 14 was vacuum-dried. When the content of water was determined as 0.8%, crystal C was obtained. The total amount of residual solvent in crystal A was determined as 0.4% (mass percentage) by GC (Gas Chromatography).

Comparative Example 2

Effects of Different Solvents on the Crystal Forms of the Compound of Formula I

At 25° C., 0.8 g of the compound of formula I in amorphous form prepared in Example 1 were dissolved into 5 ml of an, aqueous methanol solution (methanol:water=3:2). The resultant solution was slowly cooled to 0° C., crystals precipitated from the solution, and the system was stirred for 3 hours at this temperature. A solid amorphous powder was obtained by filtration.

Comparative Example 3

Effects of Different Solvents on the Crystal Forms of the Compound of Formula I

At 32° C. 2.1 g of the compound of formula I in amorphous form prepared in Example 1 were dissolved into 50 ml of an aqueous ethanol solution (ethanol:water=5:1). The resultant solution was slowly cooled to 10° C., crystals precipitated from the solution, and the system was stirred for 5 hours at this temperature. A solid amorphous powder was obtained by filtration.

Comparative Example 4

Effects of Different Solvents on the Crystal Forms of the Compound of Formula I

At 20° C., 3 g of the compound of formula I in amorphous form prepared in Example 1 were dissolved into 55 ml of an aqueous n-propanol solution (n-propanol:water=1:1). The resultant solution was slowly cooled to 0° C., crystals precipitated from the solution, and the system was stirred for 5 hours at this temperature. A solid amorphous powder was obtained by filtration, Comparative Example 5

Effects of Different Solvents on the Crystal Forms of the Compound of Formula I

At 45° C., 2.5 g of the compound of formula I in amorphous form prepared in Example 1 were dissolved into 32 ml of an aqueous isopropanol solution (isopropanol:water=2:3). The resultant solution was slowly cooled to 15° C., crystals precipitated from the solution, and the system was stirred for 1 hour at this temperature. A solid amorphous powder was obtained by filtration.

Comparative Example 6

Effects of Different Solvents on the Crystal Forms of the Compound of Formula I

At 32° C., 1.7 g of the compound of formula I in amorphous form prepared in Example 1 were dissolved into 90 ml of an aqueous isopropanol solution (isopropanol:water=4:1). The resultant solution was slowly cooled to 10° C., crystals precipitated from the solution, and the system was stirred for 2 hours at this temperature. A solid amorphous powder was obtained by filtration.

Comparative Example 7

Effects of Different Solvents on the Crystal Forms of the Compound of Formula I

At 28° C., 1 g of the compound of formula I in amorphous form prepared in Example 1 was dissolved into 50 ml of an aqueous n-butanol solution (n-butanol:water=9:1). The resultant solution was slowly cooled to 0° C., 50 ml of methyl acetate were slowly added, and A solid amorphous powder was obtained by filtration.

Comparative Example 8

Effects of Different Solvents on the Crystal Forms of the Compound of Formula I

At 17° C., 1.2 g of the compound of formula I in amorphous form prepared in Example 1 were dissolved into 45 ml of an aqueous acetone solution (acetone:water=4:1). The resultant solution was slowly cooled to −5° C., crystals precipitated from the solution, and the system was stirred for 3.5 hours at this temperature. A solid amorphous powder was obtained by filtration.

Comparative Example 9

Effects of Different Solvents on the Crystal Forms of the Compound of Formula I

At 25° C., 5 g of the compound of formula I in amorphous form prepared in Example 1 were dissolved into 150 ml of an aqueous acetonitrile solution (acetonitrile:water 3:1). The resultant solution was slowly cooled to 8° C., crystals precipitated from the solution, and the system was stirred for 2 hours at this temperature. 200 ml of isopropyl acetate were slowly added, and a solid amorphous powder was obtained by filtration.

Comparative Example 10

Effects of Different Solvents on the Crystal Forms of the Compound of Formula I

At 30° C., 1.7 g of the compound of formula I in amorphous form prepared in Example 1 were dissolved into 100 ml of an aqueous methanol/ethanol solution (methanol:

ethanol:water=8:2:1.). The resultant solution was slowly cooled to 11° C., crystals precipitated from the solution, and the system was stirred for 6 hours at this temperature, 100 ml of ethyl acetate were slowly added, and a solid amorphous powder was obtained by filtration.

Comparative Example 11

Effects of Different Solvents on the Crystal Forms of the Compound of Formula I

At 23° C., 1.7 g of the compound of formula I in amorphous form prepared in Example 1 were dissolved into 100 ml of an aqueous propanol butanol solution (propanol:butanol:water=6:5:3). The resultant solution was slowly cooled to −5° C. crystals precipitated from the solution, and the system was stirred for 7 hours at this temperature. A solid amorphous powder was obtained by filtration.

Comparative Example 12

Effects of Different Solvents on the Crystal Forms of the Compound of Formula I

At 45° C., 4 g of the compound of formula I in amorphous form prepared in Example 1 were dissolved into 28 ml of an aqueous methanol/n-butanol solution (methanol:n-butanol:water=1:7:2). The resultant solution was slowly cooled to 11° C., crystals precipitated from the solution, and the system was stirred for 6 hours at this temperature. A solid amorphous powder was obtained by filtration.

Comparative Example 13

Effects of Different Solvents on the Crystal Forms of the Compound of Formula I

At 20° C., 1 g of the compound of formula I in amorphous form prepared in Example 1 was dissolved into 70 ml of an aqueous ethanol/butanol solution (ethanol:butanol:water=2:2:5). 100 ml of ethyl acetate were slowly added, and a solid amorphous powder was obtained by filtration.

Comparative Example 14

Effects of Different Solvents on the Crystal Forms of the Compound of Formula I

At 50° C., 3 g of the compound of formula I in amorphous form prepared in Example 1 were dissolved into 20 ml of an aqueous methanol/acetonitrile solution (methanol:acetonitrile:water=4:1:2). The resultant solution was cooled to 25° C., crystals precipitated from the solution, and the system was stirred for 2 hours at this temperature. 70 ml of ethyl acetate were slowly added, and a solid amorphous powder was obtained by filtration.

Comparative Example 15

Effects of Different Solvents on the Crystal Forms of the Compound of Formula I

At 30° C., 2 g of the compound of formula I in amorphous form prepared in Example 1 were dissolved into 10 ml of an aqueous methanol/acetone solution (methanol:acetone:water=9:2:2). The resultant solution was cooled to 5° C., crystals precipitated from the solution, and the system was stirred for 4 hours at this temperature. 50 ml of ethyl acetate were slowly added, and A solid amorphous powder was obtained by filtration.

Example 19

Purity and Stability Test

In this Example, the purity and stability of the samples obtained in Comparative Examples and Examples were compared. The method used is as follows:

Crystals A-C of the compound of formula I prepared in Examples 2, 11 and 15, the crystal of B82 type obtained in Comparative Example 1 and the amorphous solid obtained in Example 1 were taken respectively and sealed at 25° C. for 30 days. And then the content of impurities in the sample was analyzed. Results of comparing the stability of crystals A-C of the compound of formula I according to the present invention, the crystal of B82 type and the amorphous solid are shown in the following table:

| Sample | Purity of initial sample | Purity of sample after stored at 25° C. for 30 days |
| --- | --- | --- |
| Crystal A | 99.68% | 99.65% |
| Crystal B | 99.55% | 99.50% |
| Crystal C | 99.64% | 99.43% |
| B82-type Crystal | 99.50% | 96.98% |
| Amorphous solid | 99.38% | 89.27% |

From the data in the table, it is clear that the stability of crystals A-C of the compound of formula I is obviously superior to that of the B82-type crystal, and is far superior to that of the amorphous solid.

Example 20

Preparation of Pharmaceutical Compositions

The preparation process was: a stabilizer was dissolved in 200 ml of water, the crystal of the compound of formula I was added and dissolved, the pH was adjusted, and the resulting mixture was added into 100 vials of 10 ml volume and lyophilized, so as to obtain pharmaceutical compositions. The formulations of the composition before lyophilization are listed in the following table:

| Number | Added crystal of the compound of formula I | Stabilizer | pH adjusting agent |
| --- | --- | --- | --- |
| 1 | Crystal A of the compound of formula I obtained according to the method of Example 2, 2.5 g | Lactose, 20 g | Anhydrous citric acid-sodium hydroxide, pH 5.5 |
| 2 | Crystal B of the compound of formula I obtained according to the method of Example 11, 2.5 g | Trehalose, 25 g | Phosphate, pH 6.0 |
| 3 | Crystal C of the compound of formula I obtained according to the method of Example 15, 2.5 g | Sucrose, 15 g | Acetate, pH 5.5 |

Example 21

Preparation of Pharmaceutical Compositions 0.2 g of crystal A of the compound of formula I obtained by the method in Example 2, 0.2 g of crystal B of the compound of formula I obtained by the method in Example 11, and 0.2 g of crystal C of the compound of formula I obtained by the method in Example 14 were prepared into eye drops respectively according to the method in Example 2 of US2007249546A1.

Characterization of Crystal A of the Compound of Formula I

Crystal A of the compound of formula I obtained in Example 2 was characterized by an X-ray powder diffractometer. There are characteristic peaks at the following 2θ angles in the X-ray diffraction pattern; 3.6°, 6.4°, 6.8°, 7.5°, 9.4°, 10.8°, 12.4°, 13.6°, 20.4°, and the X-ray power diffraction pattern is shown in FIG. 1.

Figure 2:
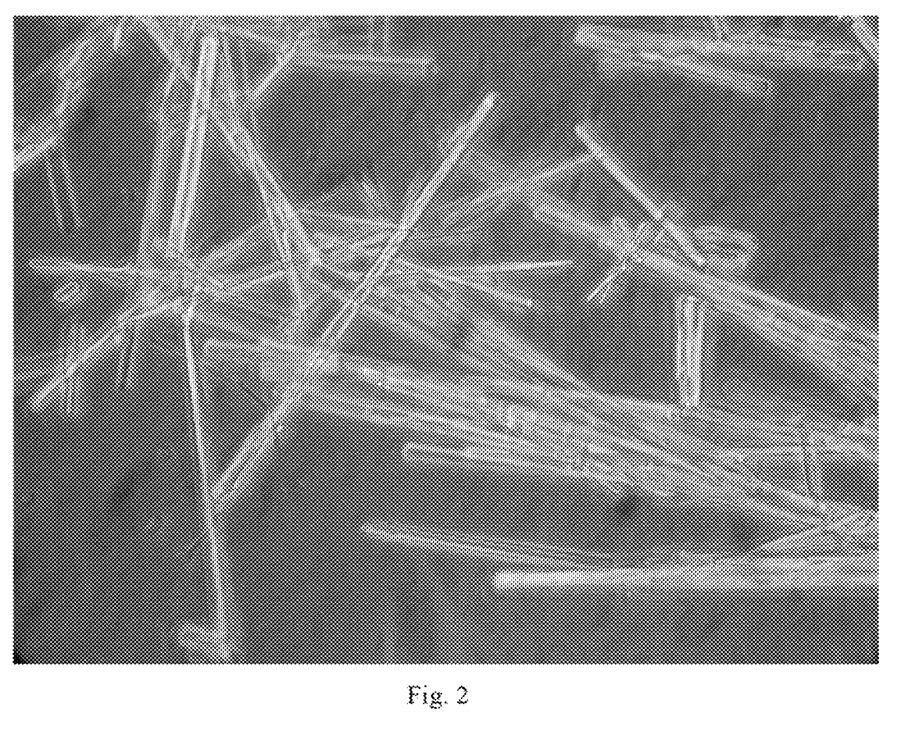
FIG. 2 shows a photograph of crystal A of the compound of formula I observed under a microscope before filtration.

Under an optical microscope, crystal A of the compound of formula I is a column-like crystal and its shape before filtration is shown in FIG. 2.

Upon examination, the structure and shape of the crystals of Examples 3-10 are identical with those of the crystal of Example 2. Therefore, the reproducibility of the method of the present invention is excellent, and the stable crystal A of the compound of formula I can be obtained.

Characterization of Crystal B of the Compound of Formula I

Crystal B of the compound of formula I obtained in Example 11 was characterized by an X-ray powder diffractometer. There are characteristic peaks at the following 2θ angles in the X-ray diffraction pattern: 4.4°, 5.2°, 7.5°, 8.5°, 8.8°, 9.6°, 12.6°, 13.7°, 14.9°, 15.7°, 16.7°, 22.5°, 25.1°, and the X-ray power diffraction pattern is shown in FIG. 3.

Crystal B of the compound of formula I obtained in Example 13 was characterized by an X-ray powder diffractometer. There are characteristic peaks at the following 2θ angles in the X-ray diffraction pattern: 4.4°, 5.1°, 7.4°, 8.4°, 8.7°, 9.5°, 12.6°, 13.6°, 14.8°, 15.5°, 16.6°, 22.4°, 25.0°, and the X-ray power diffraction pattern is shown in FIG. 4.

The IR pattern of crystal B of the compound of formula I is shown in FIG. 5, and there are characteristic peaks at the following wave numbers: 3340.16 cm$^{-1}$, 2954.82 cm$^{-1}$, 2874.54 cm$^{-1}$, 2364.47 cm$^{-1}$, 2083.34 cm$^{-1}$, 1625.74 cm$^{-1}$, 1505.84 cm$^{-1}$, 1416.10 cm$^{-1}$, 1389.34 cm$^{-1}$, 1255.82 cm$^{-1}$, 1178.41 cm$^{-1}$, 1114.04 cm$^{-1}$, 1085.09 cm$^{-1}$, 1046.10 cm$^{-1}$, 965.79 cm$^{-1}$, 838.03 cm$^{-1}$, 770.45 cm$^{-1}$, 752.44 cm$^{-1}$, 802.51 cm$^{-1}$, 715.64 cm$^{-1}$, 612.14 cm$^{-1}$, 583.00 cm$^{-1}$, 505.24 cm$^{-1}$.

Upon examination, the structure of the crystals of Examples 12-14 is identical with that of the crystal of Example 11. Therefore, the reproducibility of the method of the present invention is excellent, and the stable crystal B of the compound of formula I can be obtained.

Characterization of Crystal C of the Compound of Formula I

Crystal C of the compound of formula I obtained in Example 15 was characterized by an X-ray powder diffractometer. There are characteristic peaks at the following 2θ angles in the X-ray diffraction pattern: 4.5°, 5.2°, 8.5°, 9.6°, and the X-ray power diffraction pattern is shown in FIG. 6.

Upon examination, the structure of the crystals of Examples 16-18 is identical with that of the crystal of Example 15. Therefore, the reproducibility of the method of the present invention is excellent, and the stable crystal C of the compound of formula I can be obtained.

The embodiments described above are merely preferred embodiments of the present invention, and not provided to limit the scope of the substantial technical contents of the present invention, which are broadly defined in the claims of the present application. If any technical entity or method completed by other people is identical with that defined by the claims of the present application, or is an equivalent modification, all of them will be deemed as falling within the scope of the claims.

The invention claimed is:

1. Crystal A of a cyclic peptide compound of formula I:

formula I wherein said crystal A has characteristic peaks at the following 2θ angles in the X-ray power diffraction pattern (XRPD): 3.6±0.2°, 6.4±0.2°, 6.8±0.2°, and 9.5±0.2°.

2. The crystal A of the cyclic peptide compound according to claim 1, wherein said crystal A has additional characteristic peaks at the following 2θ angles in the X-ray power diffraction pattern (XRPD): 7.5±0.2°, 11.0±0.2°, and 12.4±0.2°.

3. The crystal A of the cyclic peptide compound according to claim 2, wherein said crystal A has additional characteristic peaks at the following 2θ angles in the X-ray power diffraction pattern (XRPD): 13.4±0.2° and 20.2±0.2°.

4. Crystal B of a cyclic peptide compound of formula I:

formula I wherein said crystal B has characteristic peaks at the following 2θ angles in the X-ray power diffraction pattern (XRPD): 4.4±0.2°, 5.2±0.2°, 8.5±0.2°, and 9.6±0.2°.

5. The crystal B of the cyclic peptide compound according to claim 4, wherein said crystal B has additional characteristic peaks at the following 2θ angles in the X-ray power diffraction pattern (XRPD): 7.5±0.2°, 8.8±0.2°, 16.6±0.2°, 13.7±0.2°, and 22.5±0.2°.

6. The crystal B of the cyclic peptide compound according to claim 5, wherein said crystal B has additional characteristic peaks at the following 2θ angles in the X-ray power diffraction pattern (XRPD): 12.6±0.2°, 14.9±0.2°, 15.6±0.2°, and 25.1±0.2°.

7. Crystal C of a cyclic peptide compound of formula I:

formula I wherein said crystal C has characteristic peaks at the following 2θ angles in the X-ray power diffraction pattern (XRPD): 4.5±0.2°, 5.3±0.2°, 8.6±0.2°, and 9.6±0.2°.

8. A preparation method for the crystal A of claim 1, comprising:
(a) dissolving the cyclic peptide compound of formula I of claim 1 in an aqueous mixed solution of alcohols;
(b) obtaining the crystal A of claim 1 by reducing the temperature and/or adding an organic solvent (i).

9. The preparation method according to claim 8, wherein the aqueous mixed solution of alcohols in step (a) contains methanol and an alcohol that is selected from a group consisting of isobutanol, isopropanol, and n-propanol.

10. The preparation method according to claim 9, wherein, in the aqueous mixed solution of alcohols in step (a), a volume ratio of methanol to the alcohol is 0.01-100.

11. The preparation method according to claim 8, wherein, in the aqueous mixed solution of alcohols in step (a), a volume ratio of alcohols to water is 0.1 to 100.

12. The preparation method according to claim 8, wherein, in step (b), the organic solvent (i) is selected from a group consisting of n-propanol, isopropanol, isobutanol, methyl acetate, ethyl acetate, n-propyl acetate, and isopropyl acetate.

13. The preparation method according to claim 8, wherein, in step (b), the temperature is reduced to −40 to 35° C.

14. The preparation method according to claim 8, wherein a volume ratio of the organic solvent (i) added in step (b) to the aqueous mixed solution of alcohols in step (a) is 0.1 to 50.

15. A preparation method for the crystal B of the cyclic peptide compound according to claim 4, comprising steps of:
obtaining crystal A of a cyclic peptide compound of formula I,
vacuum-drying the crystal A at the presence of a water system to control a content of water, and
obtaining the crystal B of the cyclic peptide compound according to claim 4, wherein said formula I is formula I and said crystal A has characteristic peaks at the following 2θ angles in the X-ray power diffraction pattern (XRPD): 3.6±0.2°, 6.4±0.2°, 6.8±0.2°, and 9.5±0.2°.

16. The preparation method according to claim 15, wherein the water system includes tap water, pure water, ice-water mixture, or other substances capable of releasing water vapor.

17. The preparation method according to claim 15, wherein the content of water is controlled at 4%-22%, said crystal B has characteristic peaks at the following 2θ angles in the X-ray power diffraction pattern (XRPD): 4.4±0.2°, 5.2±0.2°, 8.5±0.2°, 9.6±0.2.

18. A preparation method for the crystal C of claim 7, comprising:
obtaining crystal B of a cyclic peptide compound of formula I, said crystal B has characteristic peaks at the following 2θ angles in the X-ray power diffraction pattern (XRPD): 4.4±0.2°, 5.2±0.2°, 8.5±0.2°, 9.6±0.2°, said formula I being formula I vacuum-drying the crystal B,
controlling a content of water, and
obtaining the crystal C of claim 7.

19. The preparation method according to claim 18, wherein the content of water is controlled at less than 4%, said crystal C has characteristic peaks at the following 2θ angles in the X-ray power diffraction pattern (XRPD): 4.5±0.2°, 5.3±0.2°, 8.6±0.2°, 9.6±0.2°.

20. A method for treating fungal infections comprising administering the crystal A of the cyclic peptide compound according to claim 1.

21. A pharmaceutical composition comprising at least one of crystals A, B, and C of a cyclic peptide compound and a pharmaceutically acceptable carrier,
wherein the cyclic peptide compound is represented by formula I:

formula I said crystal A has characteristic peaks at the following 2θ angles in the X-ray power diffraction pattern (XRPD): 3.6±0.2°, 6.4±0.2°, 6.8±0.2°, and 9.5±0.2°,
said crystal B has characteristic peaks at the following 2θ angles in the X-ray power diffraction pattern (XRPD): 4.4±0.2°, 5.2±0.2°, 8.5±0.2°, and 9.6±0.2°, and
said crystal C has characteristic peaks at the following 2θ angles in the X-ray power diffraction pattern (XRPD): 4.5±0.2°, 5.3±0.2°, 8.6±0.2°, and 9.6±0.2°.

22. A preparation method for the pharmaceutical composition according to claim 21, comprising:
mixing crystals of a cyclic peptide compound shown in formula I and a pharmaceutically acceptable carrier,
wherein said crystal A has characteristic peaks at the following 2θ angles in the X-ray power diffraction pattern (XRPD): 3.6±0.2°, 6.4±0.2°, 6.8±0.2°, and 9.5±0.2°.

23. A composition of a cyclic peptide compound, comprising one or more crystals selected from a group consisting of crystals A, B, and C of the cyclic peptide compound,
wherein the cyclic peptide compound has a structural of formula I:

formula I wherein said crystal A has characteristic peaks at the following 2θ angles in the X-ray power diffraction pattern (XRPD): 3.6±0.2°, 6.4±0.2°, 6.8±0.2°, 9.5±0.2°,
said crystal B has characteristic peaks at the following 2θ angles in the X-ray power diffraction pattern (XRPD): 4.4±0.2°, 5.2±0.2°, 8.5±0.2°, and 9.6±0.2°,
said crystal C has characteristic peaks at the following 2θ angles in the X-ray power diffraction pattern (XRPD): 4.5±0.2°, 5.3±0.2°, 8.6±0.2°, and 9.6±0.2°.

24. The crystal B of the cyclic peptide compound according to claim 4, wherein said crystal B has additional characteristic peaks at the following 2θ angles in the X-ray power diffraction pattern (XRPD): 4.4±0.1°, 5.2±0.1°, 8.5±0.1°, and 9.6±0.1°.

25. The crystal B of the cyclic peptide compound according to claim 24, wherein said crystal B has additional characteristic peaks at the following 2θ angles in the X-ray power diffraction pattern (XRPD): 7.5±0.1°, 8.8±0.1°, 16.6±0.1°, and 13.7±0.1°, 22.5±0.1°.

26. The crystal B of the cyclic peptide compound according to claim 25, wherein said crystal B has additional characteristic peaks at the following 2θ angles in the X-ray power diffraction pattern (XRPD): 12.6±0.1°, 14.9±0.1°, 15.6±0.1°, and 25.1±0.1°.

27. The preparation method according to claim 10, wherein, in the aqueous mixed solution of alcohols in step (a), the volume ratio of the two alcohols is 0.05-20.

28. The preparation method according to claim 27, wherein, in the aqueous mixed solution of alcohols in step (a), the volume ratio of the two alcohols is 0.1-10.

29. The preparation method according to claim 11, wherein, in the aqueous mixed solution of alcohols in step (a), the ratio of total volume of the alcohols to the volume of water is 0.5 to 10.

30. The preparation method according to claim 29, wherein, in the aqueous mixed solution of alcohols in step (a), the ratio of total volume of the alcohols to the volume of water is 1 to 7.

31. The preparation method according to claim 13, wherein, in step (b), the temperature is reduced to −20 to 35° C.

32. The preparation method according to claim 31, wherein, in step (b), the temperature is reduced to −10 to 30° C.

33. The preparation method according to claim 32, wherein, in step (b), the temperature is reduced to −5 to 15° C.

34. The preparation method according to claim 14, wherein the volume ratio of organic solvent (i) in step (b) to the aqueous mixed solution of alcohols in step (a) is 0.1 to 10.

35. The preparation method according to claim 34, wherein the volume ratio of organic solvent (i) in step (b) to the aqueous mixed solution of alcohols in step (a) is 1-5.

* * * * *